US012723253B2

(12) United States Patent
Wang et al.

(10) Patent No.: US 12,723,253 B2
(45) Date of Patent: Sep. 1, 2026

(54) USE OF MDPHY7 PROTEIN OR MDPHY7 GENE OF APPLE IN REGULATING ANTHOCYANIN BIOSYNTHESIS

(71) Applicant: Nanjing Hejiachun Biological Technology Co., Ltd., Nanjing City (CN)

(72) Inventors: Liangju Wang, Nanjing City (CN); Liuzi Zhang, Nanjing City (CN); Jianting Zhang, Nanjing City (CN)

(73) Assignee: Nanjing Hejiachun Biological Technology Co., Ltd., Nanjing City (CN)

( * ) Notice: Subject to any disclaimer, the term of this patent is extended or adjusted under 35 U.S.C. 154(b) by 64 days.

(21) Appl. No.: 18/944,792

(22) Filed: Nov. 12, 2024

(65) Prior Publication Data

US 2026/0049325 A1 Feb. 19, 2026

(30) Foreign Application Priority Data

Aug. 13, 2024 (CN) ......................... 202411109837.X

(51) Int. Cl.
*C07K 14/415* (2006.01)
*C12N 15/82* (2006.01)

(52) U.S. Cl.
CPC .......... *C12N 15/825* (2013.01); *C07K 14/415* (2013.01); *C12N 15/8205* (2013.01)

(58) Field of Classification Search
None
See application file for complete search history.

(56) References Cited

PUBLICATIONS

Carole L. Bassett et. al., Reflective Films and Expression of Light-regulated Genes in Field-grown Apple, Journal of America Society for Horticultural Science (2014)139(4):487-494 (Year: 2014).*

Yankai Liu et al., Phytochrome interacting factor MdPIF7 modulates anthocyanin biosynthesis and hypocotyl growth in apple, Plant Physiology (2022) 188: 2342-2363 (Year: 2022).*

L. Xie et. al., 5-Aminolevulinic acid promotes anthocyanin accumulation in Fuji apples, Plant Growth Regulation (2013) 69:295-303 (Year: 2013).*

Jian-Ping An et. al., Dynamic regulation of anthocyanin biosynthesis at different light intensities by the BT2-TCP46-MYB1 module in apple, Journal of Experimental Botany (2020) vol. 71, No. 10 pp. 3094-3109 (Year: 2020).*

(Continued)

*Primary Examiner* — Weihua Fan
*Assistant Examiner* — Yanxin Shen
(74) *Attorney, Agent, or Firm* — Rothwell, Figg, Ernst & Manbeck, P.C.

(57) ABSTRACT

Disclosed is use of an MdPHY7 protein or an MdPHY7 gene related to apple anthocyanin biosynthesis in regulation of the apple anthocyanin biosynthesis, belonging to the technical field of plant genetic engineering. Exogenous 5-aminolevulinic acid (ALA) treatment can induce expression of the MdPHY7 gene, thereby promoting an increase of the apple anthocyanin biosynthesis, and then ultimately resulting in accumulation of apple anthocyanins to promote apple fruit coloring.

2 Claims, 5 Drawing Sheets

Specification includes a Sequence Listing.

(56) References Cited

PUBLICATIONS

Liuqing Huo et. al., The Apple Autophagy-Related Gene MdATG9 Confers Tolerance to Low Nitrogen in Transgenic Apple Callus, Frontiers in Plant Science (2020) vol. 11, article 423 pp. 1-14 (Year: 2020).*

Shuai Wang et. al., Phosphorylation of MdERF17 by MdMPK4 promotes apple fruit peel degreening during light/dark transitions, The Plant Cell (2022) 34: pp. 1980-2000 (Year: 2022).*

Yajun Li et. al., Establishment of virus-induced gene silencing system and functional analysis of ScbHLH17 in Senecio cruentus, Plant Physiology and Biochemistry (2020) 147, pp. 272-279 (Year: 2020).*

Carlos Alberto Silva Junior et. al., Phytochrome type B family: The abiotic stress responses signaller in plants, Annals of Applied Biology (2021)178, pp. 135-148 (Year: 2021).*

* cited by examiner

-2000 bp ATG

*GUS*

*ProMdPHY7*

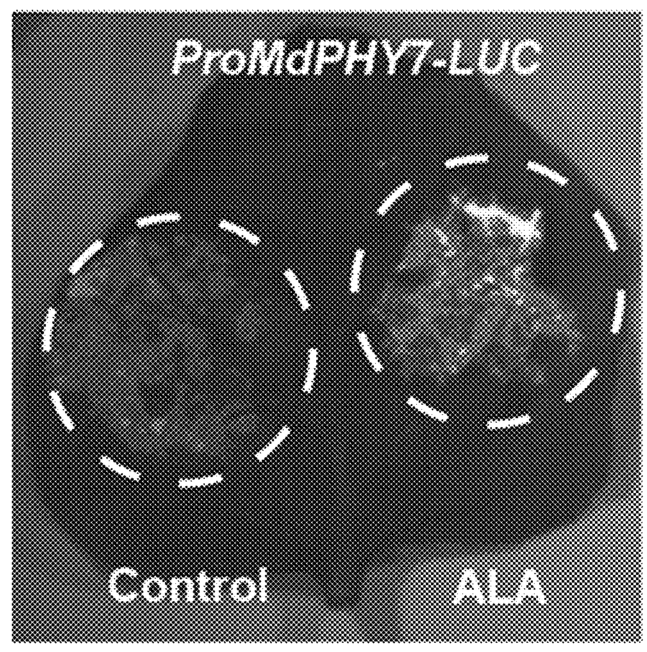
FIG. 2D
MdPHY7-GFP
Bright Chl GFP Merge
Dark
Light
FIG. 3
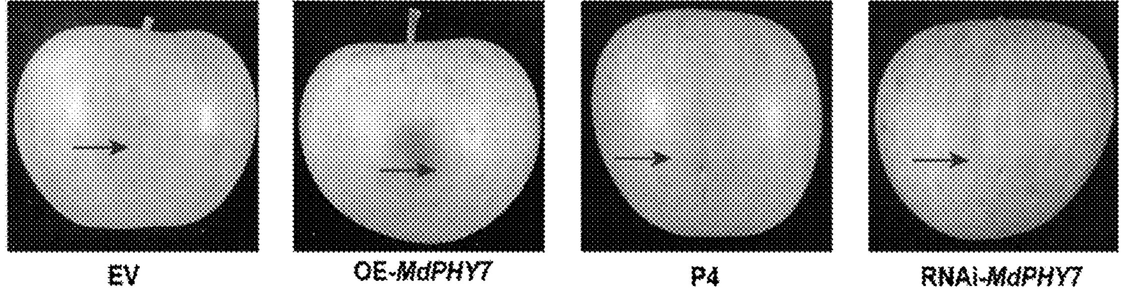
FIG. 4A

SEQUENCE LISTING

```
Sequence total quantity: 3
SEQ ID NO: 1            moltype = AA  length = 1120
FEATURE                 Location/Qualifiers
source                  1..1120
                        mol_type = protein
                        note = Malus pumila Mill
                        organism = synthetic construct
SEQUENCE: 1
MASGAQSSGT SNIKAHHNTE SVSKAIAQYT VDARLHAVFE QSGESGKSFD YSQSMKTTKD  60
SVPEQQITAY LSKIQRGGHV QPFGCMMAVD EATFGVIAYS ENARDMLDLT PQSVPILEKP  120
EILTIGTDVR TLFTPSSAVL LEKAFGAREI TLLNPIWIHS KISGKPFYAI LHRIDVGVVI  180
DLEPARTEDP ALSIAGAVQS QKLAVRAISQ LQSLPGGDIK LLCDTVVESV RELTGYDRVM  240
VYKFHEDEHG EVVAESKRPD LDPYLGLHYP ATDIPQASRF LFKQNRARMI VDCHAKPVHV  300
IQDEGLMQPL CLVGSTLRAP HGCHSQYMAN MGSIASLALA VIINGNDEEA LGGRNSMRLW  360
GLVVCHHTSA RCIPFPLRYA CEFLMQAFGL QLNMELQLAS QMSEKHVLRT QTLLCDMLLR  420
DTPTGIVTQS PSIMNLVKCD GAALYYQGNY YPLGVTPTEA QIKDIVEWLL ASHGSSTGLS  480
TDSLADAGYP GAASLGDAVC GMAAAYITKR DFLFWFRSHT GKEIKWGGAK HHPEDKDDGQ  540
RMHPRSSFKA FLEVVKSRSL PWENAEMDAI HSLQIILRDS FKNTETNNTN AVMRAQLGDL  600
EFQGINELSS VAREMVRLIE TATAPILAVD VNGCINGWNA KVAELTGLSV EEATGKSLVH  660
DLIYKESEEI VEKLLTRALK GEEDKNVEIK MRTFGPEHDN KPVFIVVNAC SSKDYANNMV  720
GVCFVGQDVT GQKVIMDKFI KIQGDYKAIV HSPNPLIPPI FASDDNTCCS EWNTAMEKLT  780
GWNQGEILGK MLVGEVFGSC CRIKGPDAMT KFMIVLHNAI GGLDTDKFPF SFFDRNGKYV  840
QALLTANKRV DTEGQVIGAF CFLQIASPEL QQTLKVQKQQ ENECLSRMKE LAYICQEVKN  900
PLSGIRFTNS LLEATDLTED QKQFLETSAA CEKQILKIIK DVDLDSIDDG SLELEKTGFL  960
LGSVINAVVS QVMLLLRERD LQLIRDIPEE IKTLAVYGDQ VRIQQVLADF LLNMVRYAPS  1020
PEGWVEIHVL PSLKKVPDGI TLVHTEFRLA CPGEGLPPQL VQDMFHSSQW MTQEGLGLSM  1080
CTKILKLMNG EVQYVRESER CYFLITLELP MPRRPTNSID                        1120

SEQ ID NO: 2            moltype = DNA  length = 3363
FEATURE                 Location/Qualifiers
source                  1..3363
                        mol_type = other DNA
                        note = Malus pumila Mill
                        organism = synthetic construct
SEQUENCE: 2
atggcgtcag gagctcagtc gtcgggcacg agcaatatca aggctcacca caacacggag  60
tctgtgagca aagccattgc tcagtacact gtagatgctc ggctgcacgc cgtgttcgag  120
cagtccgggg agtccggcaa gtcgttcgac tactcgcaga gcatgaaaac caccaaagat  180
tccgtcccgg agcagcagat tacggcgtac ctgtcgaaga ttcagagggg cggccatgtc  240
caacctttcg ggtgcatgat ggccgtggac gaagccacgt tcggagtcat tgcgtatagc  300
gagaacgcac gcgacatgct cgacctaacg ccgcagtcag tgccgatcct tgaaaagccg  360
gagattctca caattgggac cgacgtccgt acgctattca caccgtcgag cgcggtgttg  420
ctggagaagg catttggggc tcgggagata accctttttga acccgatttg gatccactct  480
aagatttctg gaaagccctt ttacgcaatt ttgcatagga ttgatgttgg ggtcgtgatt  540
gatttggagc ctgcgagaac agaagaccct gcgctgtcga ttgccggcgc ggtgcagtcg  600
cagaagctgg cggtgagggc gatttcgcag ctgcagtcgc tgccgggcgg cgacattaag  660
cttttgtgtg acactgtggt agagagtgtg agggagctta ctggctatga tagagttatg  720
gtttataagt ttcacgagga tgagcatggt gaggttgtgg ctgagagtaa aaggcctgac  780
ttggacccat accttgggct gcactacccg gccacggata taccacaggc gtcaaggttc  840
ttgttcaagc agaaccgggc tcgaatgata gtagattgtc acgccaagcc ggttcatgtg  900
attcaggatg aagggctgat gcagcctttg tgcttggttg gatccacact aagagcccca  960
catggttgcc attcccagta catggctaat atgggatcca ttgcgtcatt ggcgttggcg  1020
gtaatcatca atggaaacga cgaggaagct cttggtggga gaaattcaat gagattatgg  1080
ggcctggttg tttgccatca cacctctgct cggtgcattc catttccgct tcggtatgct  1140
tgtgagtttt taatgcaggc ctttggactt caattgaata tggaattaca attggcttca  1200
caaatgtctg agaaacatgt tttaaggaca cagactctgt tgtgtgatat gcttctgcgt  1260
gataccccaa ctggcattgt tactcaaagt cctagtataa tgaaccttgt gaaatgtgat  1320
ggggctgcac tctactacca agggaactac taccctcttg gtgtgacgcc caccgaagcc  1380
cagataaagg acattgtgga gtggttgttg gcttcccatg gaagttcaac tggtttgagt  1440
acagatagtt tggctgatgc cgggtaccct ggagctgcct ctcttggtga tgcagtttgt  1500
```

-continued

```
ggaatggcgg ctgcttatat tactaaaagg gattttctgt tctggttccg atcccacact  1560
gggaaagaga tcaaatgggg tggagcaaag catcatccag aggacaagga tgatgggcag  1620
aggatgcatc cacgctcttc attcaaagcg tttttggaag tggttaaaag ccggagcttg  1680
ccatgggaga atgcagaaat ggatgcaata cactctttgc agattatttt gcgtgactca  1740
tttaagaaca cagagacaaa caatacaaat gctgttatgc gggcccagct tggcgatctg  1800
gagtttcaag ggatcaatga gctcagctcc gtagcaagag aaatggttag gttgatagag  1860
actgcaactg ctcccatact tgctgtcgat gttaatggct gtataaatgg gtggaatgca  1920
aaggttgcag agttgaccgg tctctcagtt gaggaagcta ccgggaagtc cttggttcac  1980
gatctcattt acaaagaatc tgaagaaatt gttgaaaaac ttctaacccg cgctttaaaa  2040
ggtgaagaag ataagaatgt cgaaatcaaa atgaggacat ttggcccaga gcatgataac  2100
aagcctgtct tcatagtggt taatgcttgc tctagcaagg attacgctaa taacatggtt  2160
ggagtttgct ttgttggtca ggacgttact ggtcaaaaag taataatgga caaattcata  2220
aaaatacaag gtgattacaa agccattgtt catagcccca atcctttgat ccctcccata  2280
tttgcttcag atgataacac atgttgctcg gaatggaaca ctgccatgga aaagctcact  2340
gggtggaacc agggagaaat ccttggaaaa atgttggttg gagaggtctt cggcagttgc  2400
tgtcgaatca agggtccaga tgctatgaca aaattcatga ttgtcttgca caatgccatt  2460
ggagggctag acacagacaa attccccttt tcgttctttg accggaatgg gaaatatgta  2520
caagctctct tgacagcaaa taagagggtg gatacagaag gtcaggttat tggagctttc  2580
tgctttttgc agattgctag tccggaactg cagcaaactc ttaaagtaca gaagcaacaa  2640
gaaaatgaat gtttatctag gatgaaagaa ttggcttaca tttgccagga agtaaaaaat  2700
cctttaagtg gtatacgctt tactaactca cttttggagg ctacggactt aactgaagac  2760
caaaagcagt ttctggagac tagtgctgct tgtgagaagc aaattttgaa gattataaaa  2820
gatgttgatc tggatagcat tgacgatgga tcactggagc ttgagaagac aggattctta  2880
cttgggagcg ttataaacgc tgttgttagc caagtaatgt tattgctcag agaaagagat  2940
ctacaattga ttcgagatat tcctgaagaa atcaaaacat tggccgtcta tggtgatcaa  3000
gtgagaattc aacaggtctt ggctgatttc ttattgaata tggtacgtta tgcaccctct  3060
cctgaaggct gggtggagat tcatgttctt ccaagcttga agaaagtacc ggatggaatc  3120
actctggttc atactgaatt caggttggca tgtcctggcg aaggtctccc tcctcaatta  3180
gttcaagaca tgttccatag cagtcaatgg atgactcagg aaggtcttgg actgagcatg  3240
tgcacgaaga ttttaaagct catgaacggt gaagtccaat atgtcagaga gtcagaaaga  3300
tgttatttct taattactct tgagcttcct atgcctcgga gacctacaaa tagtattgac  3360
tag                                                                3363

SEQ ID NO: 3            moltype = DNA  length = 500
FEATURE                 Location/Qualifiers
source                  1..500
                        mol_type = other DNA
                        note = Malus pumila Mill
                        organism = synthetic construct
SEQUENCE: 3
atggcgtcag gagctcagtc gtcgggcacg agcaatatca aggctcacca caacacggag  60
tctgtgagca aagccattgc tcagtacact gtagatgctc ggctgcacgc cgtgttcgag  120
cagtccgggg agtccggcaa gtcgttcgac tactcgcaga gcatgaaaac caccaaagat  180
tccgtcccgg agcagcagat tacggcgtac ctgtcgaaga ttcagagggg cggccatgtc  240
caacctttcg ggtgcatgat ggccgtggac gaagccacgt tcggagtcat tgcgtatagc  300
gagaacgcac gcgacatgct cgacctaacg ccgcagtcag tgccgatcct tgaaaagccg  360
gagattctca caattgggac cgacgtccgt acgctattca caccgtcgag cgcggtgttg  420
ctggagaagg catttggggc tcgggagata accctttga acccgatttg gatccactct  480
aagatttctg gaaagccctt                                          500
```

USE OF MDPHY7 PROTEIN OR MDPHY7 GENE OF APPLE IN REGULATING ANTHOCYANIN BIOSYNTHESIS

CROSS REFERENCE TO RELATED APPLICATION

This patent application claims the benefit and priority of Chinese Patent Application No. 202411109837.X filed with the China National Intellectual Property Administration on Aug. 13, 2024, the disclosure of which is incorporated by reference herein in its entirety as part of the present application.

REFERENCE TO SEQUENCE LISTING

A computer readable XML file entitled "Sequence Listing.xml" that was created on Oct. 10, 2024, with a file size of 9,016 bytes, contains the sequence listing for this application, has been filed with this application, and is hereby incorporated by reference in its entirety.

TECHNICAL FIELD

The present disclosure belongs to the technical field of plant genetic engineering, and in particular relates to use of an MdPHY7 protein or an MdPHY7 gene of apple in regulating anthocyanin biosynthesis.

BACKGROUND

Anthocyanins play a key role in the coloring process of apples, with their content directly affecting the vibrancy of the color of apple peels. In addition, in terms of nutritional value, anthocyanin is a natural antioxidant that shows significant benefits to human health, including anti-cancer, cardiovascular protection, and improvement of obesity and diabetes. Therefore, in-depth research on the regulation mechanism of anthocyanin biosynthesis is of great significance for improving the quality of apple fruits, promoting the sustainable development of the apple industry, and rural revitalization.

5-aminolevulinic acid (ALA), as a novel natural plant growth regulator, has been shown to have a significant effect on promoting the accumulation of anthocyanins in fruits such as apple (*Malus domestica*), pear (*Pyrus* spp.), and peach (*Prunus persica*). The ALA has a great application potential in the field of fruit production.

However, there are no reports on the involvement of phytochrome (PHY) members in ALA-regulating apple anthocyanin accumulation.

SUMMARY

A purpose of the present disclosure is to provide use of an MdPHY7 protein or an MdPHY7 gene of apple in regulating anthocyanin biosynthesis. Exogenous ALA treatment can induce expression of the MdPHY7 gene, thereby promoting an increase of the apple anthocyanin biosynthesis.

The present disclosure provides use of the MdPHY7 protein or the MdPHY7 gene in regulation of apple anthocyanin biosynthesis; where the amino acid sequence of the MdPHY7 protein is set forth in SEQ ID NO: 1; and the nucleotide sequence of the MdPHY7 gene is set forth in SEQ ID NO: 2.

In some embodiments, the regulation of apple anthocyanin biosynthesis includes positive regulation to promote the apple anthocyanin biosynthesis and negative regulation to inhibit the apple anthocyanin biosynthesis.

In some embodiments, sites for the regulation of apple anthocyanin biosynthesis include the peel, leaves, and callus tissue of apple.

The present disclosure further provides a method for promoting apple anthocyanin biosynthesis, including the following steps: infecting an apple tissue with a recombinant *Agrobacterium* strain carrying an overexpression vector; where the overexpression vector is inserted with MdPHY7 gene; and the nucleotide sequence of the MdPHY7 gene is set forth in SEQ ID NO: 2.

The present disclosure further provides an apple anthocyanin biosynthesis-related MdPHY7 gene fragment having the nucleotide sequence set forth in SEQ ID NO: 3.

The present disclosure further provides an interfering recombinant plasmid inserted with the MdPHY7 gene fragment.

The present disclosure further provides use of the MdPHY7 gene fragment or the interfering recombinant plasmid in inhibiting apple anthocyanin biosynthesis.

The present disclosure further provides a method for inhibiting apple anthocyanin biosynthesis, including the following steps: infecting an apple tissue with a recombinant *Agrobacterium* strain carrying the interfering recombinant plasmid.

The present disclosure further provides use of the MdPHY7 protein or MdPHY7 gene related to apple anthocyanin biosynthesis, the MdPHY7 gene fragment, the interfering recombinant plasmid, or the method in producing apple germplasms with different anthocyanin contents.

The present disclosure further provides use of ALA in increasing a transcriptional activity of an MdPHY7 promoter and/or promoting expression of an MdPHY7 gene; where the nucleotide sequence of the MdPHY7 gene is set forth in SEQ ID NO: 2.

The present disclosure provides use of the MdPHY7 protein or the MdPHY7 gene in regulation of apple anthocyanin biosynthesis, where the MdPHY7 protein or the MdPHY7 gene can positively regulate the accumulation of apple anthocyanins. Exogenous 5-aminolevulinic acid (ALA) treatment can induce expression of the MdPHY7 gene, thereby promoting an increase of the apple anthocyanin biosynthesis, and then ultimately resulting in accumulation of apple anthocyanins to promote apple fruit coloring. It has been verified that overexpression of the MdPHY7 gene (OE-MdPHY7) can promote the accumulation of the apple anthocyanins; while interfering with the expression of the MdPHY7 gene (RNAi-MdPHY7) can inhibit the accumulation of the apple anthocyanin, thereby inhibiting the improvement of fruit appearance quality. In summary, the MdPHY7 gene is a new key gene regulating the accumulation of the apple anthocyanin, and plays a key role in regulation of apple anthocyanin accumulation by ALA. This discovery is of far-reaching significance for agricultural and forestry production, providing a robust theoretical cornerstone for the integration of ALA into agronomic applications.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those skilled in the art without creative efforts.

FIG. 1 shows the results of the effect of ALA treatment on the coloring of apple fruit peel;

FIGS. 2A-2D show the activation effect of ALA treatment on the MdPHY7 promoter; where FIG. 2A shows the structure of ProMdPHY7:GUS vector; FIG. 2B shows that ALA promotes the enhancement effect of GUS staining; FIG. 2C shows the structure of ProMdPHY7:LUC vector; and FIG. 2D shows that ALA promotes the enhancement effect of LUC fluorescence;

FIG. 3 shows the results of subcellular localization analysis of MdPHY7-GFP in the dark and under light;

FIGS. 4A-4C show the effects of MdPHY7 overexpression or inhibition on anthocyanin accumulation in apple fruit, leaves, and callus; where in FIG. 4A, the empty vector (EV) and OE-MdPHY7 represent that fruits are continuously illuminated for 3 d in a light incubator, and P4 and RNAi-MdPHY7 represent that fruits are continuously illuminated for 5 d; in FIG. 4B, the leaves are illuminated for 3 d; and in FIG. 4C, the callus is illuminated for 14 d.

DETAILED DESCRIPTION OF THE EMBODIMENTS

Figures 1, 2A:
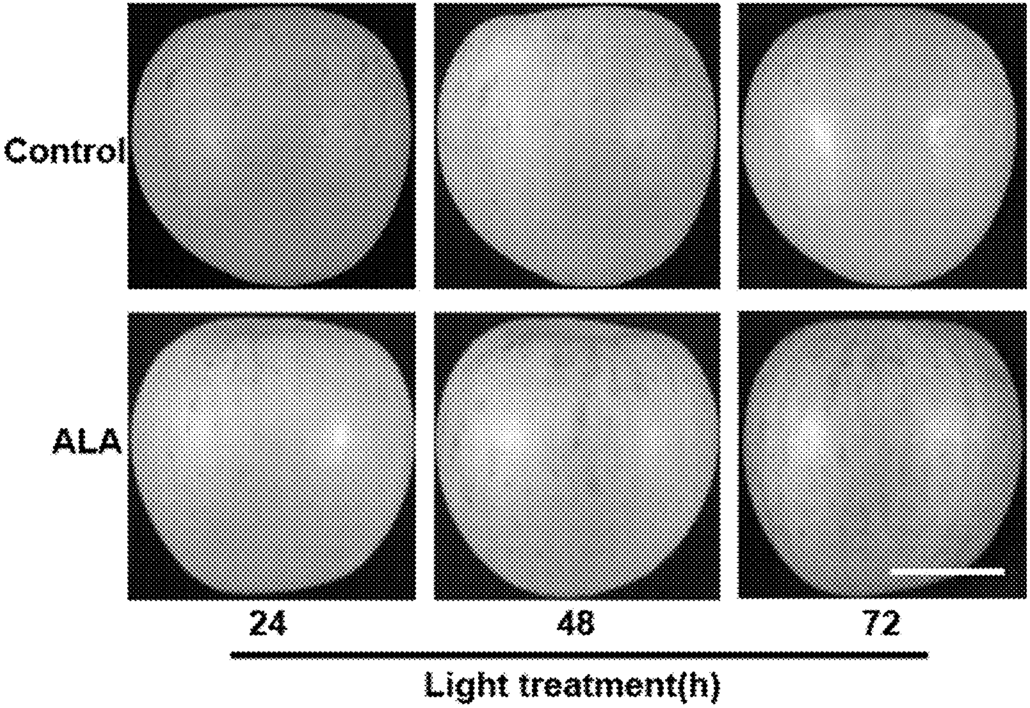

The present disclosure provides use of the MdPHY7 protein or MdPHY7 gene in regulation of apple anthocyanin biosynthesis.

In the present disclosure, the amino acid sequence of the MdPHY7 protein is set forth in SEQ ID NO: 1, specifically:

```
MASGAQSSGTSNIKAHHNTESVSKAIAQYTVDARLHAVFEQSGESGKSFD

YSQSMKTTKDSVPEQQITAYLSKIQRGGHVQPFGCMMAVDEATFGVIAYS

ENARDMLDLTPQSVPILEKPEILTIGTDVRTLFTPSSAVLLEKAFGAREI

TLLNPIWIHSKISGKPFYAILHRIDVGVVIDLEPARTEDPALSIAGAVQS

QKLAVRAISQLQSLPGGDIKLLCDTVVESVRELTGYDRVMVYKFHEDEHG

EVVAESKRPDLDPYLGLHYPATDIPQASRFLFKQNRARMIVDCHAKPVHV

IQDEGLMQPLCLVGSTLRAPHGCHSQYMANMGSIASLALAVIINGNDEEA

LGGRNSMRLWGLVVCHHTSARCIPFPLRYACEFLMQAFGLQLNMELQLAS

QMSEKHVLRTQTLLCDMLLRDTPTGIVTQSPSIMNLVKCDGAALYYQGNY

YPLGVTPTEAQIKDIVEWLLASHGSSTGLSTDSLADAGYPGAASLGDAVC

GMAAAYITKRDFLFWFRSHTGKEIKWGGAKHHPEDKDDGQRMHPRSSFKA

FLEVVKSRSLPWENAEMDAIHSLQIILRDSFKNTETNNTNAVMRAQLGDL

EFQGINELSSVAREMVRLIETATAPILAVDVNGCINGWNAKVAELTGLSV

EEATGKSLVHDLIYKESEEIVEKLLTRALKGEEDKNVEIKMRTFGPEHDN

KPVFIVVNACSSKDYANNMVGVCFVGQDVTGQKVIMDKFIKIQGDYKAIV

HSPNPLIPPIFASDDNTCCSEWNTAMEKLTGWNQGEILGKMLVGEVFGSC

CRIKGPDAMTKFMIVLHNAIGGLDTDKFPFSFFDRNGKYVQALLTANKRV

DTEGQVIGAFCFLQIASPELQQTLKVQKQQENECLSRMKELAYICQEVKN

PLSGIRFTNSLLEATDLTEDQKQFLETSAACEKQILKIIKDVDLDSIDDG

SLELEKTGFLLGSVINAVVSQVMLLLRERDLQLIRDIPEEIKTLAVYGDQ
```

-continued

```
VRIQQVLADFLLNMVRYAPSPEGWVEIHVLPSLKKVPDGITLVHTEFRLA

CPGEGLPPQLVQDMFHSSQWMTQEGLGLSMCTKILKLMNGEVQYVRESER

CYFLITLELPMPRRPTNSID.
```

In the present disclosure, the MdPHY7 protein contains 1,120 amino acids and is located on chromosome 16 of the apple genome, and has a molecular weight of 124.06 kDa, an isoelectric point of 5.5, an extinction coefficient of 0.812, and an instability coefficient of 41.63. In the amino acid composition, leucine (Leu) and alanine (Ala) are the most abundant, accounting for 10.3% and 7.4%, respectively. The protein has an overall average hydropathic index of −0.124, indicating a hydrophilic protein. Subcellular localization analysis has showed that the MdPHY7 protein is localized in the cytoplasm in the dark and in the nucleus under light.

In the present disclosure, the nucleotide sequence of the MdPHY7 gene is set forth in SEQ ID NO: 2, specifically:

```
atggcgtcaggagctcagtcgtcgggcacgagcaatatcaaggctcacca

caacacggagtctgtgagcaaagccattgctcagtacactgtagatgctc

ggctgcacgccgtgttcgagcagtccggggagtccggcaagtcgttcgac

tactcgcagagcatgaaaaccaccaaagattccgtcccggagcagcagat

tacggcgtacctgtcgaagattcagaggggcggccatgtccaacctttcg

ggtgcatgatggccgtggacgaagccacgttcggagtcattgcgtatagc

gagaacgcacgcgacatgctcgacctaacgccgcagtcagtgccgatcct

tgaaaagccggagattctcacaattgggaccgacgtccgtacgctattca

caccgtcgagcgcggtgttgctggagaaggcatttggggctcgggagata

acccttttgaacccgatttggatccactctaagatttctggaaagccctt

ttacgcaattttgcataggattgatgttggggtcgtgattgatttggagc

ctgcgagaacagaagaccctgcgctgtcgattgccggcgcggtgcagtcg

cagaagctggcggtgagggcgatttcgcagctgcagtcgctgccgggcgg

cgacattaagcttttgtgtgacactgtggtagagagtgtgagggagctta

ctggctatgatagagttatggtttataagtttcacgaggatgagcatggt

gaggttgtggctgagagtaaaaggcctgacttggacccataccttgggct

gcactacccggccacggatataccacaggcgtcaaggttcttgttcaagc

agaaccgggctcgaatgatagtagattgtcacgccaagccggttcatgtg

attcaggatgaagggctgatgcagcctttgtgcttggttggatccacact

aagagccccacatggttgccattcccagtacatggctaatatgggatcca

ttgcgtcattggcgttggcggtaatcatcaatggaaacgacgaggaagct

cttggtgggagaaattcaatgagattatggggcctggttgtttgccatca

cacctctgctcggtgcattccatttccgcttcggtatgcttgtgagtttt

taatgcaggcctttggacttcaattgaatatggaattacaattggcttca

caaatgtctgagaaacatgttttaaggacacagactctgttgtgtgatat

gcttctgcgtgataccccaactggcattgttactcaaagtcctagtataa

tgaaccttgtgaaatgtgatggggctgcactctactaccaagggaactac

taccctcttggtgtgacgcccaccgaagcccagataaaggacattgtgga
```

-continued

```
gtggttgttggcttcccatggaagttcaactggtttgagtacagatagtt
tggctgatgccgggtaccctggagctgcctctcttggtgatgcagtttgt
ggaatggcggctgcttatattactaaaagggattttctgttctggttccg
atcccacactgggaaagagatcaaatggggtggagcaaagcatcatccag
aggacaaggatgatgggcagaggatgcatccacgctcttcattcaaagcg
tttttggaagtggttaaaagccggagcttgccatgggagaatgcagaaat
ggatgcaatacactctttgcagattattttgcgtgactcatttaagaaca
cagagacaaacaatacaaatgctgttatgcgggcccagcttggcgatctg
gagtttcaagggatcaatgagctcagctccgtagcaagagaaatggttag
gttgatagagactgcaactgctcccatacttgctgtcgatgttaatggct
gtataaatgggtggaatgcaaaggttgcagagttgaccggtctctcagtt
gaggaagctaccgggaagtccttggttcacgatctcatttacaaagaatc
tgaagaaattgttgaaaaacttctaacccgcgctttaaaaggtgaagaag
ataagaatgtcgaaatcaaaatgaggacatttggcccagagcatgataac
aagcctgtcttcatagtggttaatgcttgctctagcaaggattacgctaa
taacatggttggagtttgctttgttggtcaggacgttactggtcaaaaag
taataatggacaaattcataaaaatacaaggtgattacaaagccattgtt
catagccccaatcctttgatccctcccatatttgcttcagatgataacac
atgttgctcggaatggaacactgccatggaaaagctcactgggtggaacc
agggagaaatccttggaaaaatgttggttggagaggtcttcggcagttgc
tgtcgaatcaagggtccagatgctatgacaaaattcatgattgtcttgca
caatgccattggagggctagacacagacaaattccccttttcgttctttg
accggaatgggaaatatgtacaagctctcttgacagcaaataagagggtg
gatacagaaggtcaggttattggagctttctgctttttgcagattgctag
tccggaactgcagcaaactcttaaagtacagaagcaacaagaaaatgaat
gtttatctaggatgaaagaattggcttacatttgccaggaagtaaaaaat
cctttaagtggtatacgctttactaactcacttttggaggctacggactt
aactgaagaccaaaagcagtttctggagactagtgctgcttgtgagaagc
aaattttgaagattataaaagatgttgatctggatagcattgacgatgga
tcactggagcttgagaagacaggattcttacttgggagcgttataaacgc
tgttgttagccaagtaatgttattgctcagagaaagagatctacaattga
ttcgagatattcctgaagaaatcaaaacattggccgtctatggtgatcaa
gtgagaattcaacaggtcttggctgatttcttattgaatatggtacgtta
tgcaccctctcctgaaggctgggtggagattcatgttcttccaagcttga
agaaagtaccggatggaatcactctggttcatactgaattcaggttggca
tgtcctggcgaaggtctccctcctcaattagttcaagacatgttccatag
cagtcaatggatgactcaggaaggtcttggactgagcatgtgcacgaaga
ttttaaagctcatgaacggtgaagtccaatatgtcagagagtcagaaaga
tgttatttcttaattactcttgagcttcctatgcctcggagacctacaaa
tagtattgactag.
```

In the present disclosure, during studying the accumulation of anthocyanins induced by ALA in apple, the gene MdPHY7 encoding the plant light receptor protein phytochrome 7 is isolated, cloned, and screened from the apple peel. The MdPHY7 gene can promote the apple anthocyanin biosynthesis. The accession number of MdPHY7 gene is MD16G1153800 in the Genome Database for Rosaceae (GDR), with a CDS length of 3,363 bp.

In the present disclosure, the regulation of apple anthocyanin biosynthesis preferably includes positive regulation to promote the apple anthocyanin biosynthesis and negative regulation to inhibit the apple anthocyanin biosynthesis.

In the present disclosure, the site for the regulation of apple anthocyanin biosynthesis preferably includes a peel, a leaf, and a callus of an apple. The MdPHY7 gene can be used to regulate the accumulation of anthocyanins in apple peel, thereby improving the appearance quality of apple fruit.

The present disclosure further provides a method for promoting apple anthocyanin biosynthesis, including the following steps: infecting an apple tissue with a recombinant *Agrobacterium* strain carrying an overexpression vector; where the overexpression vector is inserted with an MdPHY7 gene; and the of the MdPHY7 gene is set forth in SEQ ID NO: 2.

In the present disclosure, the overexpression vector is named OE-MdPHY7; a backbone plasmid of the overexpression vector is preferably pCAMBIA1300; an insertion site of the MdPHY7 gene on the backbone plasmid is preferably between XbaI and BamHI; a promoter for the expression of the MdPHY7 gene is preferably the 35S promoter.

In the present disclosure, an original strain of the recombinant *Agrobacterium* strain is preferably an *Agrobacterium* EHA105 or LBA4404 strain.

In the present disclosure, the overexpression is preferably transient expression.

In the present disclosure, the overexpression vector is transformed into an apple material through *Agrobacterium*, thus promoting the accumulation of anthocyanins in apple.

The present disclosure further provides an apple anthocyanin biosynthesis-related MdPHY7 gene fragment with the nucleotide sequence set forth in SEQ ID NO: 3, specifically:

```
atggcgtcaggagctcagtcgtcgggcacgagcaatatcaaggctcacca
caacacggagtctgtgagcaaagccattgctcagtacactgtagatgctc
```

-continued

```
ggctgcacgccgtgttcgagcagtccggggagtccggcaagtcgttcgac
tactgcagagcatgaaaaccaccaaagattccgtcccggagcagcagatt
acggcgtacctgtcgaagattcagaggggcggccatgtccaacctttcgg
gtgcatgatggccgtggacgaagccacgttcggagtcattgcgtatagcg
agaacgcacgcgacatgctcgacctaacgccgcagtcagtgccgatcctt
gaaaagccggagattctcacaattgggaccgacgtccgtacgctattcac
accgtcgagcgcggtgttgctggagaaggcatttggggctcgggagataa
ccctttttgaacccgatttggatccactctaagatttctggaaagccctt.
```

The present disclosure further provides an interfering recombinant plasmid inserted with the MdPHY7 gene fragment.

In the present disclosure, the backbone plasmid of the interfering recombinant plasmid is preferably an RNA interference vector pHELLSGATE4; an insertion site of the MdPHY7 gene fragment on the backbone plasmid is preferably between attP1 and attP2. The interfering with the expression of the MdPHY7 gene (RNAi-MdPHY7) can inhibit the accumulation of the apple anthocyanins, thereby inhibiting an improvement on an appearance quality of the apple fruit.

The present disclosure further provides use of the MdPHY7 gene fragment or the interfering recombinant plasmid in inhibiting apple anthocyanin biosynthesis.

The present disclosure further provides a method for inhibiting apple anthocyanin biosynthesis, including the following steps: infecting an apple tissue with a recombinant *Agrobacterium* strain carrying the interfering recombinant plasmid.

In the present disclosure, the interfering expression vector RNAi-MdPHY7 is transformed into an apple material to inhibit the accumulation of apple anthocyanins.

The present disclosure further provides use of the MdPHY7 protein or MdPHY7 gene related to apple anthocyanin biosynthesis, the MdPHY7 gene fragment, the interfering recombinant plasmid, or the method in producing apple germplasms with different anthocyanin contents.

In the present disclosure, the cultivars of the apple are preferably “Orin” and “Gala”.

The present disclosure further provides use of ALA in increasing a transcriptional activity of an MdPHY7 promoter and/or promoting expression of an MdPHY7 gene; where the nucleotide sequence of the MdPHY7 gene is set forth in SEQ ID NO: 2.

In the GUS and LUC detection analysis, exogenous ALA treatment can significantly activate the MdPHY7 promoter to promote the expression of ProMdPHY7:GUS and ProMdPHY7:LUC. ALA is located upstream of the MdPHY7 gene, and the exogenous ALA treatment can activate the MdPHY7 promoter activity, promote the transcription of the MdPHY7 gene, promote the accumulation of apple anthocyanins, and then further promote fruit coloring.

In order to further describe the present disclosure, the provided use of the MdPHY7 protein or MdPHY7 gene of apple in regulating anthocyanin biosynthesis is described in detail below with reference to the accompanying drawings and examples, but the accompanying drawings and examples should not be understood as limiting the protection scope of the present disclosure.

Example 1

Previous studies have found that ALA can significantly promote the accumulation of anthocyanins in apple fruit (WANG Liangju et al., Journal of Fruit Science, 2004, 21:512-515), but the relationship between ALA promoting the accumulation of anthocyanins in apple and phytochrome have not been elucidated. In this example, uncolored bagged “Huashuo” apples were picked 120 d after full bloom, soaked in 200 mg·L$^{-1}$ ALA solution or water (Control) for 1 min, air-dried slightly, wrapped with absorbent paper, placed in a plastic box, and kept in the dark at room temperature overnight (8 h to 12 h). The absorbent paper was removed and the apples were transferred to a light incubator with a light intensity of 200 μmol m$^{-2}$ s$^{-1}$ at 17° C. for 72 h. Every 24 h, samples were taken and photographed. The results showed that ALA treatment could significantly promote the accumulation of anthocyanins in apple (Table 1, FIG. 1).

TABLE 1

Anthocyanin contents in apple peel at different time points after ALA treatment (unit: nmol · g$^{-1}$ FW)

| | Treatment time (h) | | |
|---|---|---|---|
| | 24 | 48 | 72 |
| Control group (Control) | 1.51 ± 0.06e | 7.79 ± 0.86d | 29.62 ± 0.50b |
| Treatment group (ALA) | 1.94 ± 0.22e | 22.01 ± 0.09c | 52.08 ± 1.54a |

NOTE:
the anthocyanin contents in the table were the mean ± standard error of three biological replicates. Different lowercase letters after the data indicated significant differences at the P = 0.05 level.

Total RNA was extracted from apple peels treated with 200 mg·L$^{-1}$ ALA solution or water (Control) at 24 h, 48 h, and 72 h of light exposure. After reverse transcription into cDNA, the relative expression levels of 7 members of the apple phytochrome gene family (MdPHY1-7) were determined. The results showed that only the relative expression level of MdPHY7 in apple peels continued to increase after ALA treatment, while the other members did not show significant changes (Table 2). These data suggested that MdPHY7 might be involved in ALA-induced accumulation of anthocyanins in apple peel to promote fruit coloring, while other members were not related to ALA-induced accumulation of anthocyanins in apple.

TABLE 2

Relative expression levels of apple phytochrome gene family members (MdPHY1-7) after ALA treatment at different time points

| Treatment | Time (h) | MdPHY1 | MdPHY2 | MdPHY3 | MdPHY4 | MdPHY5 | MdPHY6 | MdPHY7 |
|---|---|---|---|---|---|---|---|---|
| | | Relative expression levels of different MdPHY genes | | | | | | |
| Control group (Control) | 24 | 1.10 ± 0.01c | 1.02 ± 0.01a | 1.00 ± 0.02a | 1.00 ± 0.02a | 1.00 ± 0.01d | 1.04 ± 0.11a | 1.00 ± 0.01e |
| | 48 | 1.00 ± 0.01d | 0.36 ± 0.08b | 0.15 ± 0.01b | 0.47 ± 0.01d | 1.13 ± 0.01b | 0.13 ± 0.01bc | 1.23 ± 0.03d |
| | 72 | 1.18 ± 0.02b | 0.28 ± 0.11de | 0.04 ± 0.003c | 0.76 ± 0.01b | 1.50 ± 0.01a | 0.04 ± 0.002c | 1.51 ± 0.02c |
| Treatment group (ALA) | 24 | 1.24 ± 0.02ab | 0.19 ± 0.003d | 0.03 ± 0.01c | 0.61 ± 0.01c | 0.79 ± 0.01e | 0.19 ± 0.04bc | 1.89 ± 0.04b |
| | 48 | 0.93 ± 0.01e | 0.15 ± 0.002e | 0.01 ± 0.002c | 0.45 ± 0.01d | 0.99 ± 0.01d | 0 | 1.49 ± 0.04c |
| | 72 | 1.28 ± 0.02a | 0.21 ± 0.005c | 0.17 ± 0.02b | 0.74 ± 0.07b | 1.09 ± 0.01c | 0 | 2.11 ± 0.05a |

NOTE:
the gene expression levels in the table were the mean ± standard error of three biological replicates. The same lowercase letters after the data in the same column represented no significant difference at the P = 0.05 level.

The promoter of the apple MdPHY7 gene obtained by cloning and screening was ligated to a β-glucuronidase gene (GUS) and a luciferase reporter gene (LUC), so as to construct the ProMdPHY7:GUS (FIG. 2A) and ProMdPHY7:LUC vectors (FIG. 2C), respectively, and then transformed into *Agrobacterium.*

Figure 2B:
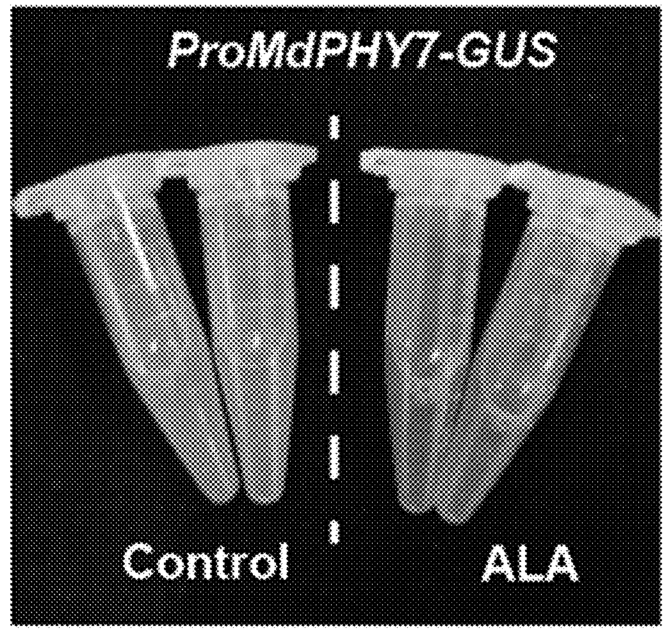
Figure 2C:
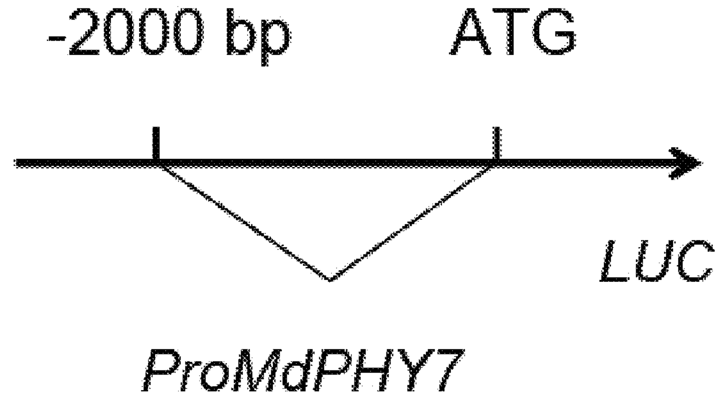
Figure 4B:
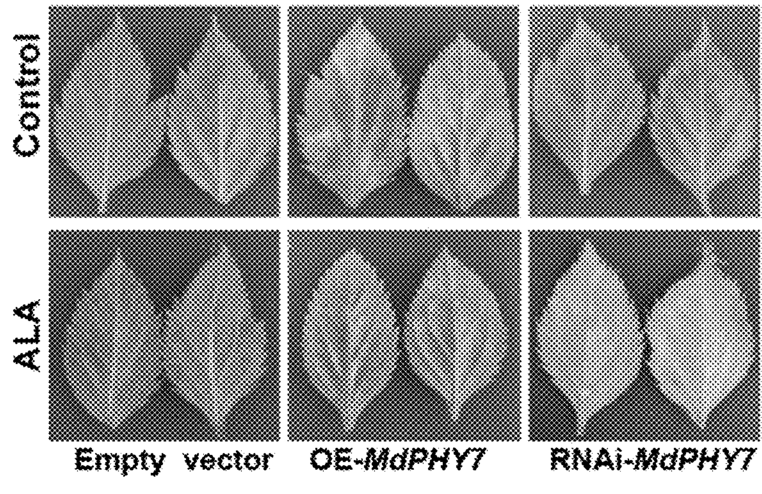
Figure 4C:
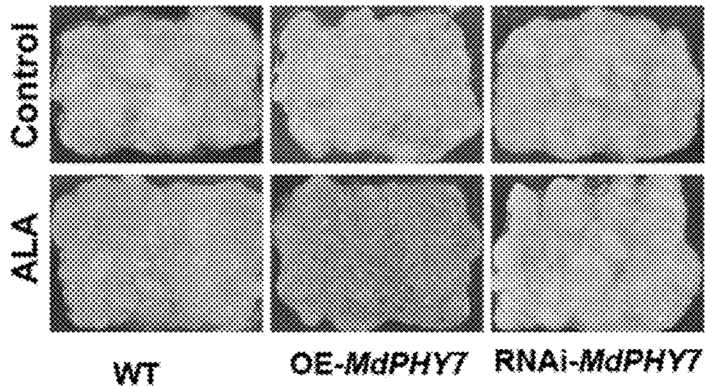

*Agrobacterium* containing the ProMdPHY7:GUS vector was transformed into the callus of the "Orin" apple to obtain a transgenic positive callus. The transgenic "Orin" callus was cultured on a Murashige & Skoog (MS) medium, where half of which contained 0.25 mg·$L^{-1}$ ALA and the other half of which did not contain ALA (Control), and then allowed to stand in the dark overnight. The callus was transferred to a 17° C., 200 μmol $m^{-2}$ $s^{-1}$ light incubator and continuously illuminated for 3 d. The apple callus tissues with different treatments were immersed in a GUS staining solution (containing 100 mM phosphate buffer, pH=7, supplemented with 0.1% (v/v) Triton X-100, 10 mM EDTA, 0.5 mM $K_3Fe(CN)_6$, 0.5 mM $K_4Fe(CN)_6$, and 1 mM 5-bromo-4-chloro-3-indole-β-D-glucuronide), allowed to stand at 37° C. for 24 h, and then placed in a centrifuge tube for photography. In addition, the total RNA from callus tissues under different treatments were extracted and reverse-transcribed into cDNA to determine the expression level of GUS gene. The results showed that the exogenous ALA treatment could activate the MdPHY7 promoter, the GUS expression level was upregulated by 141% (Table 3), and the blue appearance of callus after histochemical staining deepened (FIG. 2B). These results demonstrated that exogenous ALA could increase the activity of MdPHY7 promoter, thereby significantly increasing the expression level of GUS. The transcription of MdPHY7 in the apple was positively regulated by exogenous ALA.

TABLE 3

Relative expression levels of ProMdPHY7-GUS gene under different treatments

| Treatment | Relative expression level of GUS gene | Standard error | 1% difference | 5% difference |
|---|---|---|---|---|
| Control | 1.03 | 0.09 | B | b |
| ALA treatment | 2.41 | 0.10 | A | a |

NOTE:
the gene expression levels in the table were the mean and standard error of three biological replicates. Different uppercase and lowercase letters represented significant differences at P = 0.01 and P = 0.05 levels, respectively.

*Agrobacterium* containing the ProMdPHY7:LUC vector was injected into the entire leaf of *Nicotiana benthamiana*, where half of the leaf was treated with water as a control group (Control), while the other half of the leaf was evenly coated with 0.5 mg $L^{-1}$ ALA solution as an ALA treatment. The above different treatment groups were cultured at room temperature for about 3 d. The tobacco leaves were observed and photographed under a live imaging device, and the fluorescence intensity of different parts was measured simultaneously. The results showed that the activity of promoter MdPHY7 in the control group was relatively weak, but after ALA treatment, the fluorescence intensity increased exponentially (FIG. 2D, Table 4). This results further demonstrated that ALA was a positive regulator of the MdPHY7 promoter, promoting its transcriptional activity.

TABLE 4

| Relative fluorescence intensities of ProMdPHY7:LUC under different treatments | | | | |
|---|---|---|---|---|
| Treatment | Relative fluorescence intensity of LUC | Standard error | 1% difference | 5% difference |
| Control | 1.00 | 0.03 | B | b |
| ALA treatment | 2.09 | 0.03 | A | a |

NOTE:
the fluorescence intensities in the table were the mean and standard error of three biological replicates. Different uppercase and lowercase letters represented significant differences at P = 0.01 and P = 0.05 levels, respectively.

The termination codon of the screened apple MdPHY7 gene was removed, the gene was ligated to the green fluorescent protein (GFP) gene, and driven by the 35S promoter to construct a 35S::MdPHY7-GFP fusion vector, which was then transformed into *Agrobacterium* and injected into *Nicotiana benthamiana* leaves. After 2 d, the fluorescence distribution was observed under a laser confocal microscope, and it was found that the MdPHY7-GFP proteins were distributed in the cytoplasm in the dark (FIG. 3), while the MdPHY7-GFP proteins were localized in the nucleus after 6 h of light treatment. This indicated that light caused MdPHY7 to transfer to the nucleus, transmit the light signal of the external environment to the nucleus, inducing the expression of nuclear genes and the photomorphogenesis of plants.

In the present disclosure, a phytochrome gene MdPHY7 that responded to ALA treatment was selected from apple fruits treated with ALA by molecular biological methods. Through fluorescence quantification, transient transformation of apple fruits and leaves, and stable transformation of apple callus, it was found that MdPHY7 can regulate the accumulation of apple anthocyanins. Reasonable use of this gene can regulate the full coloring of apple peel, which is beneficial to the development of the apple industry.

Example 2 Overexpression of MdPHY7 in Promoting Anthocyanin Accumulation in Apple Materials and Effect of Exogenous ALA Treatment 1. Construction of Overexpression Vector of MdPHY7 (OE-MdPHY7)

The pCAMBIA1300 vector was double-digested with XbaI and BamHI restriction endonucleases to allow linearization. The MdPHY7 gene was inserted into the pCAMBIA1300 expression vector to construct 35S::MdPHY7 (OE-MdPHY7) driven by the 35S promoter. The vector was transformed into an *Agrobacterium* strain EHA105 or LBA4404 by freeze-thaw method.

2. OE-MdPHY7 Transient Transformation in Promoting Anthocyanin Accumulation in Apple Peel

*Agrobacterium* containing empty vector (EV) and overexpression vector 35S::MdPHY7 was inoculated into LB (Luria-Bertani) liquid medium containing 100 mg·L$^{-1}$ Kan (kanamycin) and 100 mg·L$^{-1}$ rifampicin. The culture was conducted by shaking at 28° C. and 200 rpm until the $OD_{600\ nm}$ value of the bacterial solution reached about 0.5. The bacterial cells were separated by centrifugation, the supernatant was removed, and the bacterial cells were resuspended in a buffer containing 10 mM magnesium chloride, 10 mM 2-(4-morpholino) ethanesulfonic acid, and 120 μM acetosyringone. The *Agrobacterium* was injected into the peel of “Huashuo” apple using a disposable syringe. The apples were placed in a dark environment for 24 h after injection. Then they were transferred to a light incubator with a light intensity of 200 μmol m$^{-2}$ s$^{-1}$ and continuously illuminated for 3 d. During this period, the accumulation of anthocyanins at the injection site was observed and photographed every 24 h. The relative expression level of MdPHY7 gene was detected by RT-PCR, and a transgenic apple material transiently overexpressing MdPHY7 (OE-MdPHY7) was obtained. The peel of the fruit plant that was instantaneously injected with the bacterial solution was sampled, and anthocyanins were extracted with a 1% (v/v) hydrochloric acid-methanol solution. The absorbance values of $OD_{530}$, $OD_{620}$, and $OD_{650}$ were measured, and the anthocyanin content was calculated. It was found that OE-MdPHY7 increased the anthocyanin content by 65% (Table 5). The results showed that overexpression of MdPHY7 gene could significantly increase the anthocyanin content in apple peel.

TABLE 5

| Anthocyanin content and relative expression level of MdPHY7 in apple peel after transient transformation with OE-MdPHY7 vector | | |
|---|---|---|
| Treatment | Anthocyanin (nmol · g$^{-1}$ FW) | Relative expression level of MdPHY7 |
| EV | 18.55 ± 0.14b | 1.00 ± 0.03b |
| OE-MdPHY7 | 30.70 ± 0.06a | 3.39 ± 0.19a |

NOTE:
the anthocyanin contents and gene expression levels in the table were the mean ± standard error of three biological replicates. Different lowercase letters after the data indicate significant differences at the P = 0.05 level.

3. OE-MdPHY7 Transient Infection of Apple Leaves in Promoting Anthocyanin Accumulation and Effect of Exogenous ALA Treatment A same infection solution as that for injecting the peel was taken, the leaves of tissue culture seedlings from 1-month-old “Gala” apple were cut and put into the infection solution containing *Agrobacterium*. The *Agrobacterium* was forced into the apple leaves using a vacuum pump (the pressure was set to −0.1 MPa, each extraction was 5 min, and repeated 2 times), and then the excess water in the leaves was absorbed with filter paper. The leaves were spread on MS solid medium containing 0.25 mg·L$^{-1}$ ALA, and MS without ALA was used as a control (Control), both of which were placed in the dark overnight. The next day, the apple leaves after different treatments were transferred to a light incubator at 17° C. and 200 μmol m$^{-2}$ s$^{-1}$ and illuminated for 3 d, and the anthocyanin content of different leaves was measured. The results showed (Table 6) that the anthocyanin content of apple leaves transformed with OE-MdPHY7 was 76.8% higher than that of EV control, and the anthocyanin content of EV leaves treated with ALA increased by 78.7%; if OE-MdPHY7 leaves were treated with exogenous ALA, the anthocyanin content was 291.6% higher than that of EV control. This demonstrates that the MdPHY7 gene can promote the accumulation of anthocyanins in apple, and exogenous ALA can further enhance the accumulation of anthocyanins in apple by promoting the expression of MdPHY7.

TABLE 6

Effect of ALA treatment on anthocyanin content in apple leaves transiently transformed with OE-MdPHY7 vector

| | Anthocyanin (nmol · g$^{-1}$ FW) | |
|---|---|---|
| Treatment | EV | OE-MdPHY7 |
| Control | 38.03 ± 0.20c | 67.24 ± 4.10b |
| ALA treatment | 67.96 ± 1.06b | 148.92 ± 3.22a |

NOTE:

the anthocyanin contents in the table were the mean ± standard error of three biological replicates. Different lowercase letters after the data indicated significant differences at the P = 0.05 level.

4. Stable Transformation of OE-MdPHY7 in "Orin" Apple Callus in Promoting Anthocyanin Accumulation and the Effect of Exogenous ALA Treatment The OE-MdPHY7 recombinant plasmid was transformed into *Agrobacterium* strain LBA4404 and then infected the callus of "Orin" apple. After kanamycin selection, a stably transformed transgenic OE-MdPHY7 apple callus was obtained. The callus was transferred to MS medium containing or not containing 0.25 mg·L$^{-1}$ ALA and cultured continuously for 14 d in an incubator at 17° C. and a light intensity of 200 μmol m$^{-2}$ s$^{-1}$. The results showed (Table 7) that the anthocyanin content in apple callus transformed with OE-MdPHY7 gene was 101% higher than that of WT control, while the anthocyanin content in callus treated with exogenous ALA alone was 102% higher than that of WT control. If OE-MdPHY7 was treated with ALA, the anthocyanin content in callus was 528.7% higher than that of WT control. This indicates that ALA is upstream of the MdPHY7 gene and regulates the accumulation of anthocyanins in apple fruit, leaves, and callus cells. Proper use of this characteristic can further enhance the effect of ALA in improving fruit quality and have an important application value in modern fruit production.

TABLE 7

Effect of ALA treatment on anthocyanin content in apple callus stably transformed with OE-MdPHY7 vector

| | Anthocyanin (nmol · g$^{-1}$ FW) | |
|---|---|---|
| Treatment | WT | OE-MdPHY7 |
| Control | 6.37 ± 0.10c | 12.82 ± 0.22b |
| ALA treatment | 12.89 ± 0.31b | 40.05 ± 0.82a |

NOTE:

the anthocyanin contents in the table were the mean ± standard error of three biological replicates. Different lowercase letters after the data indicated significant differences at the P = 0.05 level.

Example 3 Interference with MdPHY7 Gene Expression in Inhibiting Anthocyanin Accumulation in Apple and the Effect of Exogenous ALA Treatment 1. Preparation of Interfering Recombinant Plasmid P4-MdPHY7

Figure 5:
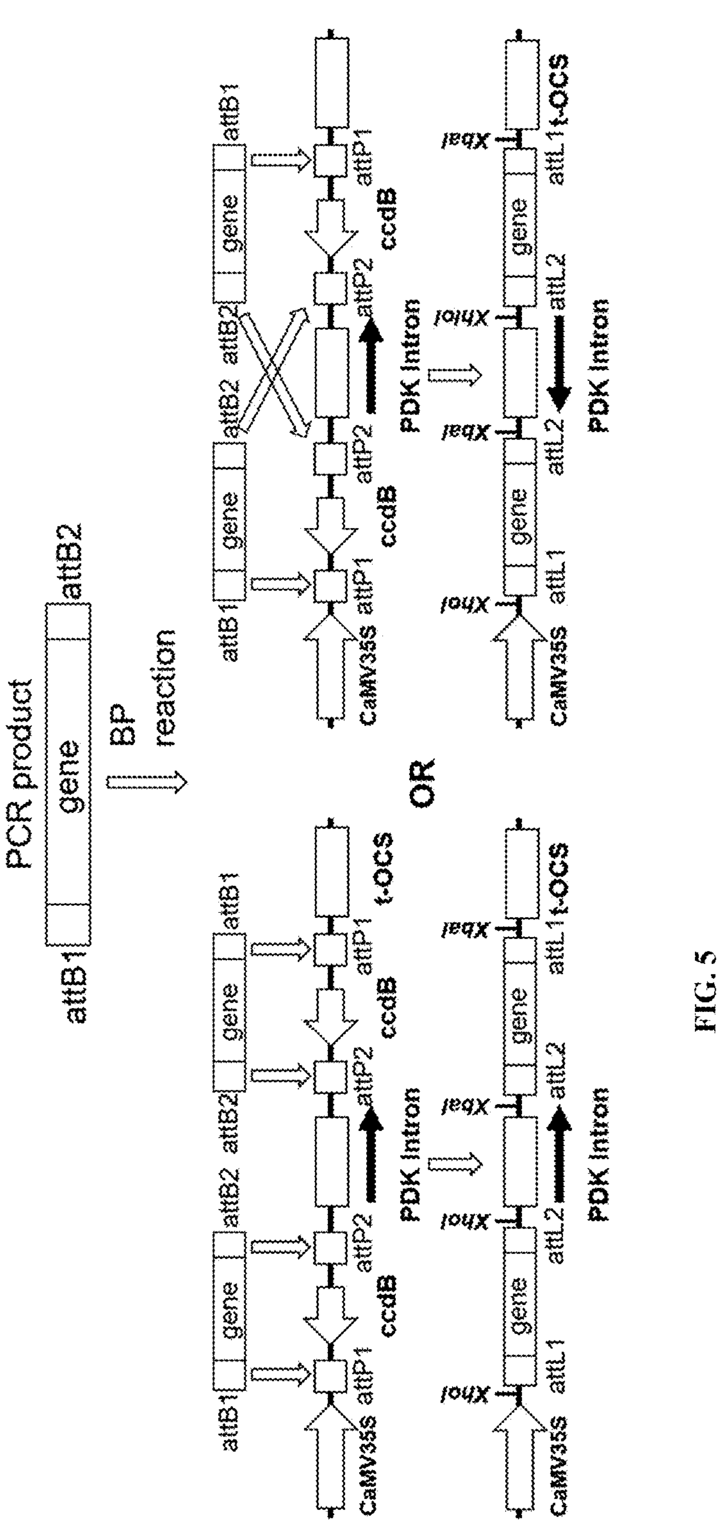
FIG. 5 shows a schematic diagram illustrating the principle of a Gateway BP recombination reaction.

To construct the RNAi-MdPHY7 vector, a specific sequence of the MdPHY7 gene was selected using the SMART online website according to the nucleotide sequence of the MdPHY7 gene:

```
atggcgtcaggagctcagtcgtcgggcacgagcaatatcaaggctcacca

caacacggagtctgtgagcaaagccattgctcagtacactgtagatgctc

ggctgcacgccgtgttcgagcagtccggggagtccggcaagtcgttcgac

tactcgcagagcatgaaaaccaccaaagattccgtcccggagcagcagat

tacggcgtacctgtcgaagattcagaggggcggccatgtccaacctttcg

ggtgcatgatggccgtggacgaagccacgttcggagtcattgcgtatagc

gagaacgcacgcgacatgctcgacctaacgccgcagtcagtgccgatcct

tgaaaagccggagattctcacaattgggaccgacgtccgtacgctattca

caccgtcgagcgcggtgttgctggagaaggcatttggggctcgggagata

acccttttgaacccgatttggatccactctaagatttctggaaagccctt.
The attB1 and attB2 site sequences (29 bp each)
```

were added to a 5'-end of the forward and reverse primers. Under the action of BP reaction recombinase, this site underwent a recombination reaction with the donor vector containing attP1 and attP2. The gene fragment was recombined into the RNA interference vector P4 (pHELLSGATE4), replacing a ccdB gene that was lethal to ordinary *Escherichia coli* strains, thus obtaining the recombinant plasmid RNAi-MdPHY7 with expression interference. This plasmid was transformed into *Agrobacterium* strain EHA105 or LBA4404. However, two construction results might occur during recombination reaction between the attB candidate gene fragment and the attP donor vector. One was the correct recombination required for the experiment, with the intron orientation unchanged. After the plant was transformed, a hairpin structure could be formed to play a splicing function (FIG. 5, left side). The other was the erroneous recombination, which was an intron-spanning reaction between attB2 and attP2, resulting in an intron orientation switch and loss of splicing function (FIG. 5, right side). Therefore, the obtained recombinant plasmid should be verified by double restriction enzyme digestion before transforming *Agrobacterium*. After the interfering recombinant plasmid RNAi-MdPHY7 was verified to be correct by restriction enzyme digestion, it was transformed into *Agrobacterium* strain EHA105 and LBA4404.

2. RNAi-MdPHY7 Transformation of Apple in Inhibiting Anthocyanin Accumulation in Apple Peel

*Agrobacterium* containing an empty vector (pHELLSGATE4, P4) and the interfering recombinant plasmid RNAi-MdPHY7 was inoculated into LB liquid medium containing 100 mg·L$^{-1}$ Kan (kanamycin) and 100 mg·L$^{-1}$ rifampicin. The culture was conducted by shaking at 28° C. and 200 rpm until an $OD_{600\ nm}$ value of the bacterial solution reached 0.5. The bacterial cells were separated by centrifugation and the supernatant was removed. The bacterial cells were resuspended in a buffer containing 10 mM magnesium chloride, 10 mM 2-(4-morpholino) ethanesulfonic acid, and 120 μM acetosyringone. The *Agrobacterium* was injected into the peel of "Huashuo" apple using a disposable syringe. After the injection, the apples were placed in a dark environment for 24 h and then transferred to a light incubator with a light intensity of 200 μmol m$^{-2}$ s$^{-1}$ and continuously illuminated. After 5 d, the accumulation of anthocyanins at the injection site was observed, photographed, and analyzed, and the relative expression level of MdPHY7 was detected by RT-PCR to verify that the expression of MdPHY7 had been interfered with. The results showed that the anthocyanin content in the peel after RNAi-MdPHY7 injection was only 41% of that in the fruit injected with P4 empty vector. Similarly, the relative expression level of MdPHY7 was only 37% of that of P4 (Table 8). This indicates that interfering with the expression of the MdPHY7 gene can inhibit the accumulation of anthocyanins in apple peel.

TABLE 8

Anthocyanin content and relative expression level of MdPHY7 in apple peel after transient transformation with RNAi-MdPHY7 vector

| Treatment | Anthocyanin (nmol · g$^{-1}$ FW) | Relative expression level of MdPHY7 |
|---|---|---|
| P4 | 71.11 ± 0.47a | 1.02 ± 0.07a |
| RNAi-MdPHY7 | 29.22 ± 0.10b | 0.38 ± 0.06b |

NOTE:
the anthocyanin contents and gene expression levels in the table were the mean ± standard error of three biological replicates. Different lowercase letters after the data indicated significant differences at the P = 0.05 level.

3. Transient Infection of Apple Leaves with RNAi-MdPHY7 in Inhibiting Anthocyanin Accumulation and Effect of Exogenous ALA Treatment A same infection solution as that for injecting the peel was taken, the leaves of tissue culture seedlings from 1-month-old "Gala" apple were cut and with the into the infection solution containing *Agrobacterium*. The *Agrobacterium* was forced into the apple leaves using a vacuum pump (the pressure was set to −0.1 MPa, each extraction was 5 min, and repeated 2 times), and then the excess water in the leaves was absorbed with filter paper. The leaves were spread on MS solid medium containing 0.25 mg·L$^{-1}$ ALA, while MS without ALA was used as a control (Control), both of which were cultured overnight in the dark. The leaves of different treatment groups were placed in a light incubator at 17° C. and 200 μmol m$^{-2}$ s$^{-1}$ for 3 d. As shown in Table 9, the anthocyanin content in apple leaves after RNAi-MdPHY7 infection was only 53.8% of that in the empty load, and exogenous ALA treatment could not reverse the decrease in anthocyanin content after MdPHY7 interference. This indicates that interfering with the MdPHY7 gene can inhibit the accumulation of anthocyanins in apple leaves and completely block the ALA-induced anthocyanin accumulation effect in apple leaves, proving that MdPHY7 was the key gene for ALA-induced anthocyanin accumulation in apple leaves. Making full use of this gene may facilitate the application of ALA in improving the quality of apple fruit.

TABLE 9

Effect of ALA treatment on anthocyanin content in apple leaves transiently transformed with RNAi-MdPHY7 vector

| | Anthocyanin (nmol · g$^{-1}$ FW) | |
|---|---|---|
| Treatment | EV | RNAi-MdPHY7 |
| Control | 38.03 ± 0.20b | 20.47 ± 0.53c |
| ALA treatment | 67.96 ± 1.06a | 24.92 ± 0.28c |

NOTE:
the anthocyanin contents in the table were the mean ± standard error of three biological replicates. Different lowercase letter after the data indicated significant differences at the P = 0.05 level.

4. RNAi-MdPHY7 Infection of "Orin" Apple Callus in Inhibiting the Anthocyanin Accumulation and Effect of Exogenous ALA Treatment The RNAi-MdPHY7 recombinant plasmid was transformed into *Agrobacterium* strain LBA4404 and then infected the callus of "Orin" apple. After kanamycin selection, a stably genetically transformed callus was obtained. The callus was transferred to MS medium containing or not containing 0.25 mg·L$^{-1}$ ALA and then cultured continuously for 14 d in an incubator at 17° C. and a light intensity of 200 μmol m$^{-2}$ s$^{-1}$. The results showed that the anthocyanin content in apple callus after RNAi-MdPHY7 gene expression interference was only 25.7% of that in the empty control. Even with exogenous ALA treatment, although the anthocyanin content in callus could be slightly increased, it still did not reach a significant level (Table 10). This again indicates that ALA is located upstream of MdPHY7 and regulates the accumulation of anthocyanins in apple. This is of important application value in improving fruit quality by ALA.

Although the above examples have described the present disclosure in detail, they are only a part of, not all of, the examples of the present disclosure. Other examples may also be obtained by persons based on the example without creative efforts, and all of these examples shall fall within the protection scope of the present disclosure.

TABLE 10

| Effect of ALA treatment on anthocyanin content in apple callus stably transformed with RNAi-MdPHY7 vector | | |
|---|---|---|
| | Anthocyanin (nmol · $g^{-1}$ FW) | |
| Treatment | WT | RNAi-MdPHY7 |
| Control | 6.37 ± 0.10b | 1.64 ± 0.14c |
| ALA treatment | 12.89 ± 0.31a | 2.42 ± 0.12c |

NOTE:
the anthocyanin contents in the table were the mean ± standard error of three biological replicates. Different lowercase letters after the data indicated significant differences at the P = 0.05 level.

What is claimed is:

1. A method for inhibiting apple anthocyanin biosynthesis, comprising the following steps: infecting an apple tissue with a recombinant *Agrobacterium* strain carrying an interfering recombinant plasmid;

wherein the interfering recombinant plasmid is inserted with an apple anthocyanin biosynthesis-related MdPHY7 gene fragment having the nucleotide sequence set forth in SEQ ID NO: 3; and wherein a backbone plasmid of the interfering recombinant plasmid is an RNA interference vector pHELLSGATE4; and an insertion site of the MdPHY7 gene fragment on the backbone plasmid is between attP1 and attP2.

2. The method according to claim 1, wherein a site for inhibiting apple anthocyanin biosynthesis is selected from the group consisting of a peel, a leaf, and a callus of an apple.

* * * * *